United States Patent [19]

Ross et al.

[11] 4,367,235

[45] Jan. 4, 1983

[54] 2-BENZIMIDAZOLINONE COMPOUNDS AND THERAPEUTIC COMPOSITIONS

[75] Inventors: Carl H. Ross, Viernheim; Walter-Gunar Friebe, Darmstadt; Wolfgang Kampe, Heddesheim; Wolfgang Bartsch, Viernheim; Egon Roesch, Mannheim, all of Fed. Rep. of Germany

[73] Assignee: Boehringer Mannheim GmbH, Mannheim-Waldhof, Fed. Rep. of Germany

[21] Appl. No.: 171,940

[22] Filed: Jul. 18, 1980

Related U.S. Application Data

[63] Continuation of Ser. No. 924,475, Jul. 13, 1978, abandoned.

[30] Foreign Application Priority Data

Aug. 12, 1977 [DE] Fed. Rep. of Germany ....... 2736295
Jan. 18, 1978 [DE] Fed. Rep. of Germany ....... 2801953

[51] Int. Cl.³ ................. A61K 31/415; C07D 235/26; C07D 235/02
[52] U.S. Cl. .............................. 424/273 B; 548/305; 548/302
[58] Field of Search ............................. 548/302, 305; 424/273 B

[56] References Cited

U.S. PATENT DOCUMENTS 4,140,789 2/1979 Jaeggi et al. ........................ 548/305

FOREIGN PATENT DOCUMENTS 2700193 7/1977 Fed. Rep. of Germany .

*Primary Examiner*—Henry R. Jiles
*Assistant Examiner*—N. Harkaway
*Attorney, Agent, or Firm*—Felfe & Lynch

[57] ABSTRACT

2-benzimidazolinone compounds of the formula

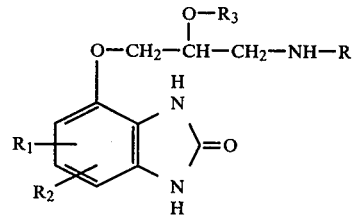

wherein
  R is lower alkyl,
  $R_1$ and $R_2$, which can be the same or different, are lower straight-chained or branched alkyl and one of $R_1$ and $R_2$ can also be hydrogen or
  $R_1$ and $R_2$ together represent an alkylene radical and $R_3$ is hydrogen or acyl, i.e., alkanoyl or aromatic carboxylic acid moieties;

and the pharmacologically acceptable salts thereof; have marked β-receptor blocking action and are outstandingly useful in the treatment or prophylaxis of cardiac and circulatory diseases.

12 Claims, No Drawings

2-BENZIMIDAZOLINONE COMPOUNDS AND THERAPEUTIC COMPOSITIONS

This is a continuation, of application Ser. No. 924,475, filed July 13, 1978, now abandoned.

The present invention is concerned with new 4-hydroxy-2-benzimidazolinone compounds, to therapeutic compositions containing them, and to methods for the treatment of cardiac and circulatory diseases utilizing such compounds.

German patent specification No. 2,700,193 describes 4-hydroxy-2-benzimidazolinone derivatives having an unsubstituted fused benzene ring, which exhibits β-receptor blocking action.

We have now found that 4-hydroxy-2-benzimidazolinone derivatives, the fused benzene ring of which is substituted one or more times by lower alkyl radical or by an alkylene bridge, exhibits a still better β-receptor blocking action and are, therefore, outstandingly useful for the treatment or prophylaxis of cardiac and circulatory diseases.

The new 4-hydroxy-2-benzimidazolinone derivatives according to the present invention are compounds of the formula:

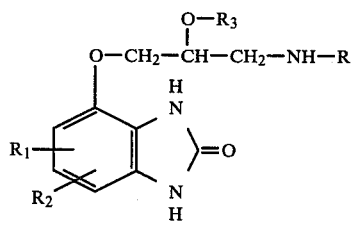

(I)

wherein
R is lower alkyl,
$R_1$ and $R_2$, which can be the same or different, are lower straight-chained or branched alkyl and $R_1$ and $R_2$ together represent an alkylene radical and $R_3$ is hydrogen or acyl, i.e., alkanoyl or aromatic carboxylic acid moieties;
and the pharmacologically acceptable salts thereof.

In the aminopropoxy side chain, the compounds of general formula (I) contain an optically-active carbon atom and can, therefore, occur not only in racemic form but also in two optically-active forms. Consequently, the present invention also includes not only the racemic forms but also the optical isomers.

The lower alkyl groups which occur in the definitions of the substituents R, $R_1$ and $R_2$ can contain 1 to 6 and preferably 1 to 4 carbon atoms, the methyl, isopropyl and tert.-butyl radicals being especially preferred.

When $R_1$ and $R_2$ together represent an alkylene radical, this contains 2 to 4 carbon atoms.

The acyl radicals $R_3$ can be acid residues derived from straight-chained or branched aliphatic carboxylic acids containing 2 to 6 carbon atoms or from aromatic carboxylic acids optionally substituted by halogen atoms, lower alkyl radicals or lower alkoxy radicals. The preferred acyl radicals include the acetyl, pivaloyl and benzoyl radicals. The aromatic carboxylic acid moiety may contain up to 10 carbon atoms in the aromatic moiety and up to 6 carbon atoms in the carboxylic acid moiety.

The new compounds, as well as their pharmacologically acceptable salts, bring about an inhibition of adrenegic β-receptors and can, therefore, be used for the treatment or prophylaxis of cardiac and circulatory diseases.

The new compounds of general formula (I) according to the present invention can be prepared, for example, by one of the following methods:

(a) reaction of a compound of the general formula:

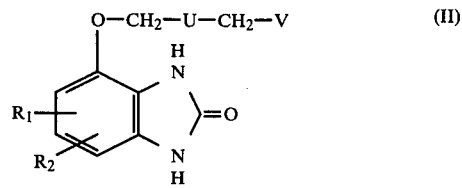

with a compound of the general formula:

wherein R, $R_1$ and $R_2$ have the same meanings as above and U stands for the group $>C=O$ or $>CH-OZ$, Z having the same meaning as $R_3$ or, together with V, representing a single bond, and one of the residues V and W is an amino group, while the other one is a reactive residue and, when U is a $>C=O$ group, the product obtained is subsequently reduced; or (b) reaction of a compound of the general formula:

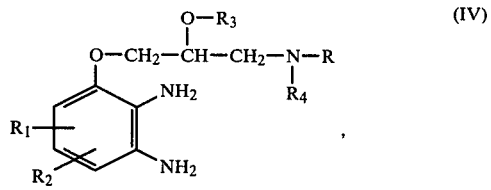

with a compound of the general formula:

wherein R, $R_1$, $R_2$ and $R_3$ have the same meanings as above, $R_4$ is a hydrogen atom or a protective group which can be split off and $Y_1$ and $Y_2$, which can be the same or different, are reactive residues, whereafter, when a protective group $R_4$ *is present, it is again split off*; or (c) reaction of a compound of the general formula:

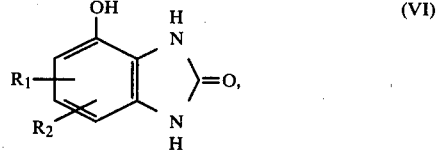

with a compound of the general formula:

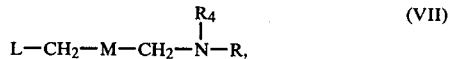

wherein R, $R_1$, $R_2$ and $R_4$ have the same meanings as above, M stands for the group $>C=O$ or $>CH-OZ$, Z having the same meaning as $R_3$ or, togeher with L, forming a single bond and L is a reactive residue, whereafter, when M stands for $>C=O$, the product obtained is subsequently reduced and when a protective group $R_4$ is present, this is split off again;

whereafter, if desired, a compound obtained of general formula (I) is subsequently converted into a pharmacologically acceptable salt, and, if desired, a compound obtained in which $R_3$ is a hydrogen atom is previously acylated on the hydroxyl group.

$Y_1$ and $Y_2$ in compounds of general formula (V) stand for all residues which are able to react with the two primary amino groups in compounds of general formula (IV) to form an imidazoline ring. Such residues are preferably halogen atoms, such as bromine or chlorine atoms, or amino, imidazolyl, lower alkoxy, lower acyloxy and phenoxy radicals. Thus, for example, a compound of general formula (V) can be a carbonyl halide, urea or N,N'-carbonyldiimidazole.

The processes according to the present invention are preferably carried out in a solvent which is inert under the reaction conditions, for example, water, ethanol, dioxan or dimethylformamide, optionally in the presence of an acid-binding agent. The reactions can also be carried out, after mixing the reaction components, without the use of a solvent. The reactions can be performed by leaving the reaction mixture to stand at ambient temperature or with heating, optionally under a protective gas atmosphere.

When it is necessary to carry out the reduction of a $>C=O$ group, this can be performed by catalytic hydrogenation with the use of a noble metal or nickel catalyst or by means of a complex metal hydride, for example sodium borohydride.

The protective group which can easily be split off, can, in principle, be any protective group which is employed in peptide chemistry for the intermediate protection of amino groups and which can be removed again after the reaction has been completed. In the case of the present reactions according to processes (b) and (c), it is especially advantageous to use benzyl or carbobenzoxy radicals which, after the reaction of compounds of general formulae (IV) and (VI) with compounds of general formulae (V) and (VII), respectively, can readily be split off hydrogenolytically in known manner.

The compounds of general formula (IV) can be prepared, for example, by reacting compounds of the general formula:

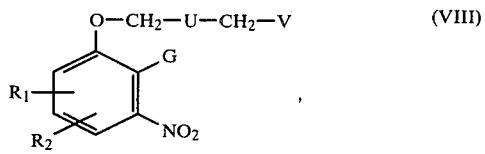

(VIII)

wherein $R_1$, $R_2$, U and V have the same meanings as above and G is an amino or nitro group, with compounds of general formula (III) analogously to process (a), whereafter the product obtained is reduced. The reduction can be carried out in known manner, preferably by catalytic hydrogenation. The crude o-phenylenediamine derivatives of general formula (IV) thus obtained are advantageously employed, without further purification, in the form of mineral acid salts as starting materials in process (b).

The compounds of general formula (VIII) are either known compounds or can easily be prepared from known compounds by known methods.

The subsequent acylation of compounds of general formula (I), in which $R_3$ is a hydrogen atom, which is possibly to be carried out can take place in the usual manner by reaction with a reactive acid derivative, for example an acid halide, acid azide or acid anhydride, optionally in the presence of an acid-binding agent, for example pyridine, in a solvent, for example acetone, benzene, dimethylformamide or also in excess acid.

The compounds of general formula (I) according to the present invention can be obtained in the form of a racemic mixture. The separation of the racemate into the optically active forms is carried out in known manner via diastereomeric salts with active acids, for example, tartaric acid, malic acid or camphor-sulphonic acid.

The new compounds of general formula (I) are preponderantly obtained, under the reaction conditions of the above-described processes, in the form of acid-addition salts, for example as hydrochlorides, and can, if desired, readily be converted into the free bases by means of known methods.

For the conversion of compounds of general formula (I) into their pharmacologically compatible salts, these are reacted, preferably in an organic solvent, with an equivalent amount of an inorganic or organic acid, for example hydrochloric acid, hydrobromic acid, phosphoric acid, sulphuric acid, acetic acid, citric acid or maleic acid.

For the preparation of pharmaceutical compositions, the compounds (I) are mixed in known manner with appropriate pharmaceutical carrier substances and aroma, flavouring and colouring materials and formed, for example, into tablets or dragees or, with the addition of appropriate adjuvants, suspended or dissolved in water or in an oil, for example olive oil.

The new compounds of general formula (I) according to the present invention and the salts thereof can be administered enterally or parenterally in liquid or solid form. As injection medium, it is preferred to use water which contains the additives usual in the case of injection solutions, such as stabilizing agents, solubilizing agents and/or buffers. Additives of this type include, for example, tartrate and citrate buffers, ethanol, complex formers (such as ethylenediaminetetraacetic acid and the non-toxic salts thereof) and high molecular weight polymers (such as liquid polyethylene oxide) for viscosity regulation. Solid carrier materials can be, for example, starch, lactose, mannitol, methyl cellulose, talc, highly-dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening agents.

Preferred compounds according to the present invention, apart from those described in the Examples, include the following compounds: 7-tert.-butyl-4-(2-hydroxy-3-tert.-butylaminopropoxy)-2-benzimidazolinone and 4-(2-pivaloyloxy-3-tert.-butylaminopropoxy)-6-methyl-2-benzimidazolinone.

The following Examples are given for the purpose of illustrating the present invention. They illustrate some of the numerous possible process variants which can be used for the synthesis of the new compounds according to the present invention.

EXAMPLE 1

4-(2-Hydroxy-3-tert.-butylaminopropoxy)-6-methyl-2-benzimidazolinone

A moderate stream of phosgene is passed into a solution of 5.8 g. 2,3-diamino-1-(2-hydroxy-3-tert.-butylaminopropoxy)-5-methylbenzene trihydrochloride in 150 ml. water for about 30 minutes. After flushing with nitrogen, the reaction mixture is evaporated to dryness and the residue crystallised from ethanol to give 3.04 g. (61% of theory) 4-(2-hydroxy-3-tert.-butylaminopropoxy)-6-methyl-2-benzimidazolinone hydrochloride; m.p. 280°–281° C.

The diamino compound required as intermediate can be prepared in the following manner:

By nitration of previously acetylated 2-amino-5-methyl-phenol (m.p. 156°–158° C.) at 30° C. with nitric acid in acetic anhydride and glacial acetic acid, there is obtained 1-acetoxy-2-acetamido-3-nitro-5-methylbenzene (m.p. 163°–165° C.) which is saponified with 2 N hydrochloric acid to give 2amino-5-methyl-3-nitrophenol (m.p. 197°–199° C.). This compound is, in turn, reacted with 3-chloro-1,2-epoxypropane and 25% aqueous sodium hydroxide solution at 75° C. to give 2-(2,3-epoxypropoxy)-4-methyl-6-nitroaniline (m.p. 90°–91° C.) reaction of which with tert.-butylamine in ethanol and subsequent catalytic hydrogenation in the presence of platinum dioxide gives, after acidification with hydrochloric acid, amorphous 2,3-diamino-1-(2-hydroxy-3-tert.-butylaminopropoxy)-5-methyl-benzene trihydrochloride.

EXAMPLE 2

4-[2-Hydroxy-3-(2-propylamino)-propoxy]-6-methyl-2-benzimidazolinone

In a manner analogous to that described in Example 1, from 2,3-diamino-1-[2-hydroxy-3-(2-propylamino)-propoxy]-5-methylbenzene trihydrochloride, there is obtained 4-[2-hydroxy-3-(2-propylamino)-propoxy]-6-methyl-2-benzimidazolinone hydrochloride; m.p. 286°–288° C.

The diamine used as intermediate is obtained by reacting the 2-(2,3-epoxypropoxy)-4-methyl-6-nitroaniline described in Example 1 with 2-propylamine to give 2-[2-hydroxy-3-(2-propylamino)-propoxy]-4-methyl-6-nitroaniline, which is then subjected to catalytic hydrogenation.

EXAMPLE 3

4-(2-Hydroxy-3-tert.-butylaminopropoxy)-7-methyl-2-benzimidazolinone 8.0 g. 2,3-Diamino-1-(2-hydroxy-3-tert.-butylaminopropoxy)-4-methylbenzene trihydrochloride are dissolved in 220 ml. water. Phosgene is passed into the solution and the precipitated crystals are filtered off with suction. After recrystallisation thereof from ethanol, with the addition of active charcoal, there are obtained 3.55 g. (54% of theory) 4-(2-hydroxy-3-tert.-butylaminopropoxy)-7-methyl-2-benzimidazolinone hydrochloride, the decomposition point of which is 312° C.

The diamino compound used as intermediate can be prepared in the following manner:

2,3-Dinitro-4-methylphenol (see H. E. Dadswell and J. Kenner, J. Chem. Soc., 1927, 583) is reacted with 3-chloro-1,2-epoxypropane and 25% aqueous sodium hydroxide solution to give, in a yield of 78% of theory, 2,3-dinitro-1-(2,3-epoxypropoxy)-4-methylbenzene (m.p. 121°–123° C.). This compound is reacted in boiling ethanol with tert.-butylamine to give 2,3-dinitro-1-(2-hydroxy-3-tert.-butylaminopropoxy, 4-methylbenzene (m.p. 104°–106° C.), catalytic hydrogenation of which, in the presence of platinum dioxide, gives amorphous 2,3-diamino-1-(2-hydroxy-3-tert.-butylaminopropoxy)-4-methylbenzene trihydrochloride.

EXAMPLE 4

4-[2-Hydroxy-3-(2-propylamino)-propoxy]-7-methyl-2-benzimidazolinone

In a manner analogous to that described in Example 3, from 2,3-diamino-1-[2-hydroxy-3-(2-propylamino)-propoxy]-4-methylbenzene trihydrochloride, there is obtained 4-[2-hydroxy-3-(2-propylamino)-propoxy]-7-methyl-2-benzimidazolinone hydrochloride; m.p. 305°–307° C.

The diamine used as intermediate is prepared by reacting the 2,3-dinitro-1-(2,3-ep xypropoxy)-4-methylbezene described in Example 3 with 2-propylamine to give 2,3-dinitro-1-[2-hydroxy-3-(2-propylamino)-propoxy]-4-methylbenzene (m.p. 122°–124° C.), followed by catalytic hydrogenation thereof.

EXAMPLE 5

4-[2-Benzoyloxy-3-tert.-butylaminopropoxy]-7-methyl-2-benzimidazolinone 4-(2-Hydroxy-3-tert.-butylaminopropoxy)-7-methyl-2-benzimidazolinone (prepared from the hydrochloride (see Example 3) and methanolic sodium methylate solution) is stirred for 5 days at ambient temperature with an equimolar amount of benzoic acid azide in dimethylformamide. The crystalline precipitate obtained is mixed with ethereal hydrochloric acid and, after evaporation, recrystallised from ethanol to give 4-[2-benzoyloxy-3-tert.-butylaminopropoxy]-7-methyl-2-benzimidazolinone hydrochloride; m.p. 216°–218° C.

EXAMPLE 6

6-tert.-Butyl-4-[2-hydroxy-3-(2-propylamino)-propoxy]-2-benzimidazolinone

Excess phosgene is passed at 20° to 25° C. into a solution of 5.5 g 5-tert.-butyl-2,3-diamino-1-[2-hydroxy-3-(2-propylamino)-propoxy]-benzene trihydrochloride in 50 ml. water, then thoroughly flushed with nitrogen, evaporated and the residue taken up in isopropanol. After a short time 2.3 g. (43% of theory) crystalline 6-tert.-butyl-4-[2-hydroxy-3-(2-propylamino)-propoxy]-2-benzimidazolinone hydrochloride precipitates out; decomposition point above 280° C.

The diamino compound used as intermediate can be prepared in the following manner:

By hydrogenation of 3-tert.-butyl-6-nitrophenol in aqueous ethanolic solution in the presence of palladium-charcoal, there is obtained 6-amino-3-tert.-butylphenol (decomposition point 206°–208° C.) which, after acetylation with acetic anhydride in ethyl acetate/pyridine, gives 4-acetamido-3-acetoxy-1-tert.-butylbenzene (m.p. 109°–110° C.). Reaction of this compound with nitric acid in acetic anhydride gives 2-acetamido-3-acetoxy-5-tert.-butylnitrobenzene (m.p. 200°–201° C.), saponification of which with dilute hydrochloric acid gives 2-amino-5-tert.-butyl-3-nitrophenol (m.p. 180°–181° C.). This is then reacted with 3-chloro-1,2-epoxypropane in 2N aqueous sodium hydroxide solution to give 4-tert.-butyl-2-(2,3-epoxypropoxy)-6-nitroaniline in the form of a dark oil which is, in turn, reacted with 2-propylamine to give 4-tert.-butyl-6-nitro-2-[2-hydroxy-3-(2-propylamino)-propoxy]-aniline in the form of an amorphous hydrochloride. Hydrogenation of this compound in ethanolic solution in the presence of platinum dioxide gives 5-tert.-butyl-2,3-diamino-1-[2-hydroxy-3-(2-propylamino)-propoxy]-benzene in the form of an amorphous trihydrochloride.

EXAMPLE 7

6-tert.-Butyl-4-(2-hydroxy-3-tert.-butylaminopropoxy)-2-benzimidazolinone

In a manner analogous to that described in Example 6, from 5-tert.-butyl-2,3-diamino-1-(2-hydroxy-3-tert.-butylaminopropoxy)-benzene trihydrochloride, there is obtained 6-tert.-butyl-4-(2-hydroxy-3-tert.-butylaminopropoxy)-2-benzimidazolinone hydrochloride, which decomposes above 300° C.

The diamino compound used as intermediate can be synthesised via the following stages:

By the reaction of 4-tert.-butyl-2-(2,3-epoxypropoxy)-6-nitroaniline with tert.-butylamine, there is obtained 4-tert.-butyl-2-(-2-hydroxy-3-tert.-butylaminopropoxy)-6-nitroaniline hydrochloride, which has a decomposition composition point of 115°-120° C. Hydrogenation of this compound in ethanolic solution in the presence of platinum dioxide gives 5-tert.-butyl-2,3-diamino-1-(2-hydroxy-3-tert.-butylaminopropoxy)-benzene in the form of an amorphous trihydrochloride.

EXAMPLE 8

6,7-Dimethyl-4-(2-hydroxy-3-tert.-butylaminopropoxy)-2-benzimidazolinone

Phosgene is passed into an aqueous solution of 7.2 g. 2,3-diamino-4,5-dimethyl-1-(2-hydroxy-3-tert.-butylaminopropoxy)-benzene trihydrochloride in the manner described in the preceding Examples. The residue obtained after evaporation of the reaction mixture is recrystallised from 30 ml. ethanol, with the addition of active charcoal. After mixing with 20 ml. ethyl acetate, there is obtained 1.1 g. (17% of theory) 6,7-dimethyl-4-(2-hydroxy-3-tert.-butylaminopropoxy)-2-benzimidazolinone hydrochloride; m.p. 308°-310° C.

The diamino compound used as intermediate is synthesized in the following manner from 2-amino-4,5-dimethylphenol (see E. Diepolder, Chem. Ber., 42, 2916/1909).

This phenol compound is acetylated with acetic anhydride in ethyl acetate/pyridine to give 2-acetamido-1-acetoxy-4,5-dimethylbenzene (m.p. 156°-158° C.) which is nitrated in acetic anhydride with 100% nitric acid at 20° C. From the nitration mixture, there is isolated, in a yield of 43% of theory, 2-acetamido-1-acetoxy-4,5-dimethyl-3-nitrobenzene (m.p. 209°-211° C.). After saponification of this compound with 2 N hydrochloric acid, there is obtained 2-amino-4,5-dimethyl-3-nitrophenol (m.p. 176°-178° C.). This compound is then converted into the sodium salt by means of methanolic sodium methylate and then reacted in dioxan/dimethylformamide with excess 3-chloro-1,2-epoxypropane at 75° C. After evaporation of the reaction mixture, the residue is taken up in chloroform, treated with water and active charcoal and freed from solvent. The amorphous residue obtained of 2-amino-4,5-dimethyl-1-(2,3-epoxypropoxy)-3-nitrobenzene is reacted in boiling ethanol with tert.-butylamine to give 2-amino-4,5-dimethyl-1-(2-hydroxy-3-tert.-butylaminopropoxy)-3-nitrobenzene, which is then hydrogenated quantitatively in ethanol in the presence of platinum dioxide to give 2,3-diamino-4,5-dimethyl-1-(2-hydroxy-3-tert.-butylaminopropoxy)-benzene, which is isolated in the form of a trihydrochloride.

EXAMPLE 9

6,7-Dimethyl-4-[2-hydroxy-3-(2-propylamino)-propoxy]-2-benzimidazolinone

In a manner analogous to that described in Example 8, from 2,3-diamino-4,5-dimethyl-1-[2-hydroxy-3-(2-propylamino)-propoxy]-benzene trihydrochloride, there is synthesised 6,7-dimethyl-4-[2-hydroxy-3-(2-propylamino)propoxy]-2-benzimidazolinone hydrochloride; m.p. 338°-340° C.

The diamino compound used as intermediate is obtained by reacting 2-amino-4,5-dimethyl-1-(2,3-epoxypropoxy)-3-nitrobenzene (see Example 8) with 2-propylamine in boiling ethanol and subsequent catalytic hydrogenation.

EXAMPLE 10

4-(2-Hydroxy-3-tert.-butylaminopropoxy)-6,7-cyclopenteno-2-benzimidazolinone

In a manner analogous to that described in Example 6, from 4,5-diamino-6-(2-hydroxy-3-tert.-butylaminopropoxy)-indane trihydrochloride there is obtained 4-(2-hydroxy-3-tert.-butylaminopropoxy)-6,7-cyclopenteno-2-benzimidazolinone hydrochloride, which has a decomposition point above 280° C.

The diamino compound used as intermediate can be prepared in the following manner:

Acetylation of 6-amino-5-indanol with acetic anhydride in ethyl acetate/pyridine gives 6-acetamido-5-acetoxyindan (m.p. 157°-158° C.), reaction of which with nitric acid in acetic anhydride gives 5-acetamido-6-acetoxy-4-nitroindan (m.p. 168°-170° C.). Acid saponification of this compound with hydrochloric acid gives 6-amino-7-nitro-5-indanol (m.p. 196°-198° C.), which is then reacted with 3-chloro-1,2-epoxypropane in dilute aqueous sodium hydroxide solution to give 5-amino-6-(2,3-epoxypropoxy)-4-nitroindan in the form of a dark oil, reaction of which with tert.-butylamine gives 5-amino-6-(2-hydroxy-3-tert.-butylaminopropoxy)-4-nitroindan in the form of an amorphous hydrochloride. Hydrogenation thereof in ethanolic solution in the presence of platinum dioxide gives 4,5-diamino-6-(2-hydroxy-3-tert.-butylaminopropoxy)-indan in the form of an amorphous trihydrochloride.

The following tests were carried out to determine the cardiac β-receptor blocking activity of certain test compounds by determining the inhibition of the heart beat frequency increase induced by intravenous administration of isoprenalin (=3,4-dihydroxy-α-[(isopropylamino)-methyl]-benzylalcohol).

The test compounds representative of the invention were the following:

Compound I: 4-(2-Hydroxy-3-tert-butylaminopropoxy)-6-methyl-2-benzimidazolinone

Compound II: 4-[2-Hydroxy-3-(2-propylamino)-propoxy]-6-methyl-2-benzimidazolinone Compound III: 4-(2-Hydroxy-3-tert-butylaminopropoxy)-7-methyl-2-benzimidazolinone As comparison compound there was included:

Compound A: 1-Isopropylamino-3-(1-naphthoxy)-2-propanol (Propranolol)

These compounds were tested as follows:

The β-receptor blocking activity of the test compounds was tested on wake rabbits weighing between 2 to 3.5 kg and kept in wooden cages. EKG-electrodes were inserted into the hind quarters of the rabbits subcutaneously and the heart frequency was measured using an integrator (15 seconds) as a digital value. The test compounds were then infused through a small tube to the ear vein of the rabbits at invervals of 10 minutes in logarithmically increasing dosages and, 10 minutes after each infusion, isoprenalin was injected intravenously at 1 μg/kg.

The results are set forth in terms of inhibition of isoprenalin tachycardia, and are set forth in the table below.

TABLE

Blocking of Isoprenalin Tachycardia in Wake Rabbits

| Test Substance | Dosage mg/kg i.v. | Heartbeat Frequency (min.) $\bar{x} \pm s_{\bar{x}}$ | $DE_{250}^*$ μg/kg i.v. |
|---|---|---|---|
| Control | without Isoprenalin | 209 ± 9 | — |
| Control | with Isoprenalin | 338 ± 10 | — |
| Compound A (Propranolol) | 0.05 | 316 ± 5 | 422 ± 110 |
| | 0.1 | 285 ± 6 | |
| | 0.2 | 269 ± 7 | |
| | 0.4 | 245 ± 3 | |
| | 0.8 | 235 ± 4 | |
| | 1.6 | 222 ± 5 | |

*Interpolated dosage which limits the frequency increase to 250 beats/min.

TABLE

Blocking of Isoprenalin Tachycardia in Wake Rabbits

| Test Substance | Dosage mg/kg i.v. | Heartbeat Frequency (min.) $\bar{x} \pm s_{\bar{x}}$ | $DE_{250}^*$ μg/kg i.v. |
|---|---|---|---|
| Compound I | 0.001 | 333 ± 12 | 5.0 |
| | 0.003 | 283 ± 6 | |
| | 0.005 | 256 ± 12 | |
| | 0.010 | 210 ± 7 | |
| Compound II | 0.001 | 316 ± 8 | 4.3 ± 0.38 |
| | 0.002 | 296 ± 5 | |
| | 0.004 | 247 ± 8 | |
| | 0.016 | 214 ± 4 | |
| | 0.032 | 209 ± 6 | |
| Compound III | 0.001 | 311 ± 8 | 6.3 ± 1.24 |
| | 0.002 | 292 ± 12 | |
| | 0.004 | 266 ± 10 | |
| | 0.008 | 232 ± 10 | |
| | 0.016 | 217 ± 8 | |
| | 0.032 | 207 ± 9 | |

*Interpolated dosage which limits the frequency increase to 250 beats/min.

The above data show that the inventive compounds are already effective at a dosage much smaller than those required of the comparison substances.

The compounds according to the present invention and thus unexpectedly superior in effectiveness to known compounds and thus present a valuable contribution to the art.

The dosages of the novel compounds of the present invention depend on the age, weight, and condition of the patient being treated. Generally speaking, for adultoral administration, the preferred unit dosage of active compound with suitable pharmaceutical diluent or lubricant is 1 mg.–40 mg. four times a day. In general the oral dosage is 20–40 mg. whereas the intravenous dosage is generally 1–5 mg., four times a day.

For preparing therapeutic compositions such as tablets and other compressed formulations, the compounds can include any compatible and edible tableting material used in pharmaceutical practice as for example, corn starch, lactose, stearic acid, magnesium stearate, talc, methyl cellulose and the like.

Similarly the compounds of the present invention can be mixed with suitable adjuvants for the preparation of resorbable hard gelatin or soft capsules utilizing conventional pharmaceutical practices.

Further, the compounds can be employed in the form of their solutions or suspensions suitable for parenteral administrations.

It will be understood that the specification and examples are illustrative but not limitative of the present invention and that other embodiments within the spirit and scope of the invention will suggest themselves to those skilled in the art.

What is claimed is:

1. 2-Benzimidazolinone compound of the formula

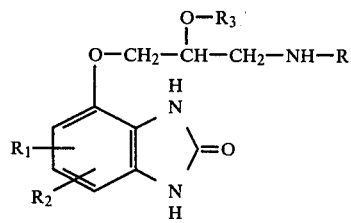

wherein
R is lower alkyl of up to 6 carbon atoms,
$R_1$ and $R_2$ together represent alkylene of from 2 to 4 carbon atoms and wherein $R_1$ and $R_2$ are in the ortho position with respect to each other, and
$R_3$ is hydrogen, alkanoyl of up to 6 carbon atoms or benzoyl
and the pharmacologically acceptable salts thereof.

2. 4-Hydroxy-2-benzimidazolinone compound as claimed in claim 1 wherein $R_3$ is hydrogen.

3. 4-Hydroxy-2-benzimidazolinone compound as claimed in claim 1 wherein $R_3$ is alkanoyl of 2 to 6 carbon atoms.

4. 2-Benzimidazolinone compound as claimed in claim 1 wherein $R_3$ is benzoyl.

5. 2-benzimidazolinone compound designated 4-(2-hydroxy-3-tert.-butylaminopropoxy)-6,7-cyclopenteno-2-benzimidazolinone.

6. 2-benzimidazolinone compound designated 4-[2-hydroxy-3-(2-propylamino)-propoxy]-6-methyl-2-benzimidazolinone.

7. 2-Benzimidazolinone compound as claimed in claim 1 wherein $R_1$ and $R_2$ are in the ortho position with respect to each other and together represent an alkylene radical of 3 carbon atoms.

8. Method of treating circulatory and cardiac diseases which method comprises administering to an afflicted subject a therapeutically effective amount of a 2-benzimidazolinone compound as claimed in claim 1.

9. Method as claimed in claim 8 wherein said compound is administered orally at a dosage of 1 mg–40 mg four times a day.

10. Method as claimed in claim 8 wherein said compound is administered orally at a dosage of 20 mg–40 mg four times a day.

11. Method as claimed in claim 8 wherein said compound is administered intravenously at a dosage of 1 mg–5 mg four times a day.

12. Therapeutic composition for the treatment of cardiac and circulatory infirmities which composition comprises a pharmacologically acceptable carrier and, in effective amounts, a 2-benzimidazolinone compound as claimed in claim 1.

* * * * *